US00PP15181P2

(12) United States Plant Patent
Danziger

(10) Patent No.: US PP15,181 P2
(45) Date of Patent: Sep. 28, 2004

(54) *GYPSOPHILA* PLANT NAMED 'DANGYPDAY'

(50) Latin Name: *Gypsophila paniculata*
Varietal Denomination: Dangypday

(75) Inventor: Gabriel Danziger, Nir-Zvi (IL)

(73) Assignee: Danziger "Dan" Flower Farm (IL)

( * ) Notice: Subject to any disclaimer, the term of this patent is extended or adjusted under 35 U.S.C. 154(b) by 0 days.

(21) Appl. No.: 10/455,451

(22) Filed: Jun. 6, 2003

(51) Int. Cl.[7] ..... A01H 5/00

(52) U.S. Cl. ..... Plt./354

(58) Field of Search ..... Plt./354

*Primary Examiner*—Kent Bell
(74) *Attorney, Agent, or Firm*—Foley & Lardner LLP

(57) ABSTRACT

A new and distinct *Gypsophila* plant named 'Dangypday' characterized by having globular shaped, semi to full double flowers (depending on growing conditions), 6–8 mm in diameter; white flower with a greenish center, symmetrical; conic, narrow flowers arranged in clusters; erect growth habit, bush, 70–90 cm in height, branching from lower part of main stem; and commercially suitable product; marketed as a cut flower.

2 Drawing Sheets

Latin name of the genus and species of the plant claimed: *Gypsophila paniculata* hybrid.
Variety denomination: 'Dangypday'.

BACKGROUND OF THE INVENTION

The present invention relates to a new and distinct cultivar of *Gypsophila* plant, botanically known as *Gypsophila paniculata,* hereinafter referred to by the cultivar name 'Dangypday'.

The new cultivar originated in a controlled breeding program through open pollination with an unknown male parent and the female parent, a hybrid line designated 'PT-2' (unpatented) in Mishmar Hashiva, Israel. 'Dangypday' was discovered and selected by the inventor, Gabriel Danziger, as a flowering plant within the progeny of the stated cross in a controlled environment in Mishmar Hashiva, Israel.

Asexual reproduction of the new cultivar by removing cutting from the initial plant was first performed in December 1999, in Mishmar Hashiva, Israel and has demonstrated that the combination of characteristics as herein disclosed for the new cultivar are firmly fixed and retained through successive generations of asexual reproduction. The instant plant reproduces true to type.

BRIEF DESCRIPTION OF THE INVENTION

The following traits have been repeatedly observed and are determined to be basic characteristics of 'Dangypday' which in combination distinguish this *Gypsophila* as a new and distinct cultivar:

1. Globular shaped, semi to full double flower (depending on growing conditions), 6–8 mm in diameter;
2. White flower with a greenish center, symmetrical;
3. Conic, narrow flowers arranged in clusters;
4. Erect growth habit, bush, 70–90 cm in height, branching from lower part of main stem; and
5. Commercially suitable product; marketed as a cut flower.

The flowers of 'Dangypday' are full and shaped like a ball. The stems are upright and notably stable. Foliage is scarce. The side stems are close to the main stem, forming several canopies of inflorescences, creating a wide and impressive structure. Both flowers of the side stems and main stems open virtually simultaneously. The plant exhibits uniform growth.

'Dangypday' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under conditions which closely approximate those generally used in commercial practice.

Of the many commercial cultivars known to the present inventor, the most similar in comparison to 'Dangypday' is the *Gypsophila* cultivar 'Dangypfirm' (U.S. Plant Pat. No. 13,564). In comparison to 'Dangypfirm', 'Dangypday' has a narrow, conic structure, branching from lower part of main stem whereas 'Dangypfirm' is of open formation, branching along main stem, has a more upright growth habit and more symmetrical flowers.

Table one provides a comparison between 'Dangypday' and the female parent 'PT-2'.

TABLE 1

| Characteristic | New cultivar 'Dangypday' | Female parent 'PT-2' |
|---|---|---|
| Flower | Semi to full double; globular; 6–8 mm diameter; white in color with greenish center; symmetrical | Semi-double; globular; 8–10 mm in diameter; white in color |
| Inflorescence | Conic. narrow flowers arranged in clusters | Conic flowers, dispersed umiformly at upper part |
| Growth Habit | Bush; 70–90 cm in height; erect, branching from lower part of main stem | Bush; 90–100 cm; erect, branching from plant base |
| Flowering Time | Early | Medium |
| Yield (stem per plant in first flash) | 7–9 | 10–12 |

BRIEF DESCRIPTION OF THE DRAWING

The accompanying photographic illustrations show the new cultivar with colors as true as possible with photographic reproductions.

The first drawing shows a flowering stem of *Gypsophila* 'Dangypday'.

The second drawing shows a close-up of of 'Dangypday' flowers.

DETAILED BOTANICAL DESCRIPTION

The following observations, measurements and values describe the new cultivar as grown in Mishmar Hashiva, Israel under conditions which closely approximate those generally used in commercial practice. Color references are made to The Royal Horticultural Society Colour Chart (R.H.S.), except where general colors of ordinary significance are used. Color values were taken under daylight conditions at approximately noon in Mishmar Hashiva, Israel. The age of 'Dangypday' when described is 12 weeks.

Propagation: Stem cutting.

Plant:

*General appearance and form.*—Height: 70–90 cm. Width: 40–50 cm. Habit: Apical dominance, branching from lower part of main stem. Form: Upright bush type, erect, narrow. Flowering Response: Long day. Flowering Season: Naturally during summer, all year with supplemental lighting. Winter Hardiness: Zone 11. Lastingness of the Individual Bloom: 10–12 days. Rooting: Use rooting hormone. Fragrance: Typical of *Gypsophila*.

Foliage:

*Overall shape of leaf.*—Lanceolate.

*Base.*—Truncate.

*Tip.*—Acuminate.

*Margin.*—Entire.

*Texture.*—Rough.

*Main color of upper surface.*—Green 137-A (both mature and immature leaves).

*Main color of lower surface.*—Green 137-B (both mature and immature leaves).

*Venation color.*—None (both surfaces).

*Size.*—Length: 6–7 cm. Width: 1–1.5 cm.

*Stipules.*—None.

*Petiole.*—4 mm in length; 5 mm width; yellow-green, RHS 145 A.

Inflorescence:

*Natural flowering season.*—Long day.

*Corolla.*—Form: Semi double to double depending on growing conditions. Shape: Globular. Average Number: 900–1000 flowers per flowering stem. Size: 6–8 mm in diameter. Petal Number: 40–60. Petal Shape: Spatulate with tip emarginated. Petal Markings: None. Petal Color: White 155-D (both surfaces). Sepal Shape: Elliptic. Apex: Acute. Margin: Entire. Sepal Length: 2 mm. Sepal Width: 1 mm. Sepal Color: Yellow-green, RHS 144 A.

*Stem.*—Average length: 70–90 cm. Average diameter: 4–5 mm. Color: Yellow-Green 143-C. Internode length: 3–4 cm.

*Spur.*—None.

*Bud.*—Response: Long day. Color: Greenish white, RHS 144 D. Size: Length: 2 mm. Width: 3 mm. Shape: Oblate. Pedicel Length: 8–10 mm. Pedicel Color: Yellow-Green 146-B.

Reproductive organs:

*Stamen.*—Number: 5–10 (seldom seen). Color: White.

*Seeds.*—Width: 1 mm. Length: 1 mm. Shape: Kidney-shaped. Color: Black-Brown.

*Fruit.*—Color: Light Brown.

*Anthers.*—5–10 (seldom seen). Color: White.

*Pollen.*—Present. Color: White.

*Stigma.*—2 pistils convex. Color: White. Ovary: .Color: Green.

Disease/pest resistance: Unknown.

I claim:

1. A new and distinct *Gypsophila* plant named 'Dangypday', substantially as illustrated and described herein.

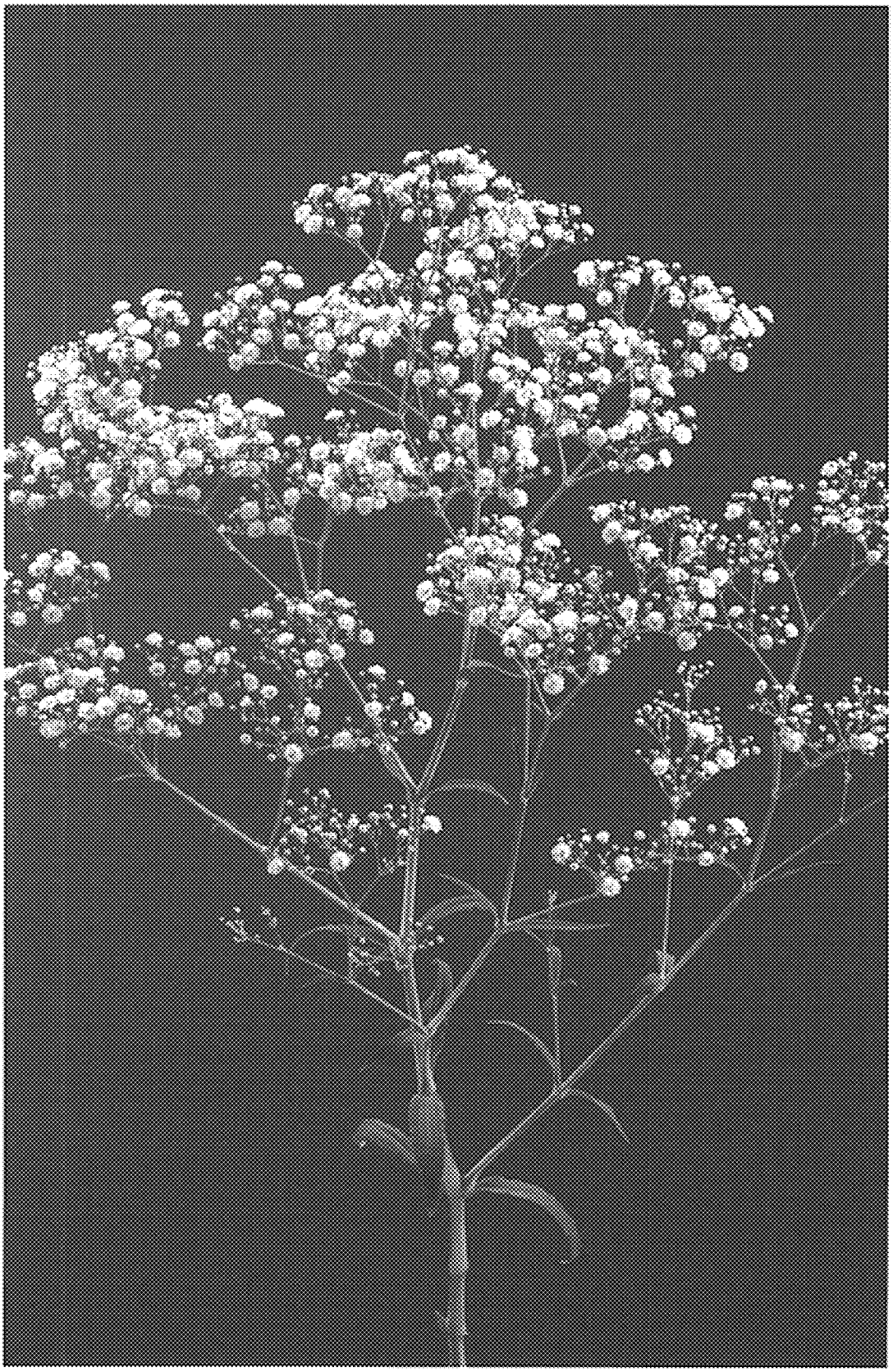

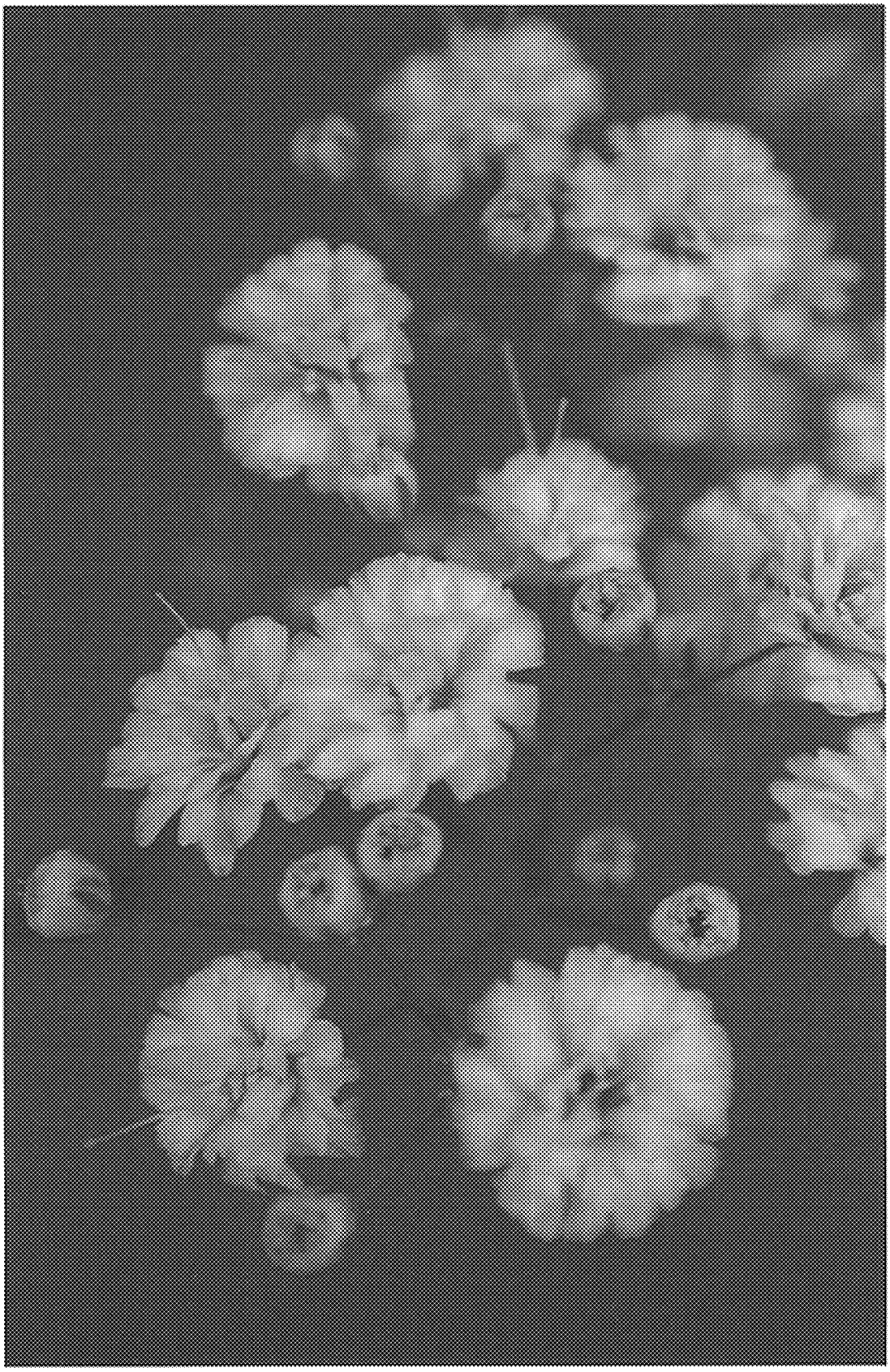

* * * * *